US005650291A

United States Patent [19]

Lee

[11] Patent Number: 5,650,291
[45] Date of Patent: Jul. 22, 1997

[54] MONOCLONAL ANTIBODIES AGAINST AN ANTIGEN ASSOCIATED WITH OVARIAN CERVICAL AND OTHER TUMORS

[75] Inventor: Chi-Yu Gregory Lee, Vancouver, Canada

[73] Assignee: The University of British Columbia, Vancouver, Canada

[21] Appl. No.: 287,068

[22] Filed: Aug. 8, 1994

Related U.S. Application Data

[63] Continuation of Ser. No. 388,032, Jul. 31, 1989, abandoned.

[51] Int. Cl.$^6$ ............................. C07K 16/30; C12N 5/20
[52] U.S. Cl. ........................ 435/344.1; 530/387.7; 530/388.8; 530/388.85; 530/391.3; 530/391.7; 435/172.2; 435/70.21; 435/344
[58] Field of Search ..................... 530/387.7, 388.8, 530/388.85, 391.3, 391.7; 435/240.27, 172.2, 70.21; 424/1.49, 183.1, 138.1, 155.1, 156.1

[56] References Cited

U.S. PATENT DOCUMENTS 4,472,371  9/1984  Burchiel et al. .
5,045,451  9/1991  Uhr et al. .

FOREIGN PATENT DOCUMENTS 0226418  6/1987  European Pat. Off. .
0226419  6/1987  European Pat. Off. .
8901629  2/1989  WIPO .

OTHER PUBLICATIONS

Poels et al., (1986) Journal of the National Cnacer Institute 76(5):781–791.
Thor et al., (1986) Journal of the National Cancer Institute 76(6):995–1006.
Pan et al., (1989) Clinical Chemistry 35(6):1081, abstract no 075.
Accola et al., (1980) Proc. Natl. Acad. Sci. USA 77:563–566.
Alvarez et al., (1987) Gynecologic Oncology 26:284–289.
Atack et al., (1986) Am. J. Obstet. Gynecol. 154:287–289.
Bara et al., (1977) Br. J. Cancer 36:49–56.
Bast et al., (1981) J. Clin. Invest. 68:1331–1337.
Bast et al., (1983) N. Engl. J. Med. 309:883–887.
Bast et al., (1984) Am. J. Obstet. Gynecol. 149:553–559.
Bhattecharya et al., (1982) Cancer Res. 42:1650–1654.
Donaldson et al., (1980) Cancer 445:948–953.
Fleuren et al., (1987) Virchows Archiva 410:481–486.
Imamura et al., (1978) Int. J. Cancer 21:570–577.
Kabawat et al., (1983) Int. J. Gynecol. Pathol. 2:275–285.
Kabawat et al., (1983) Am. J. Clin. Pathol. 79:98–104.
Kawahara et al., (1986) Cancer 58:2008–2012.
Knauf et al., (1978) Am. J. Obstet. Gynecol. 131:780–787.
Knauf et al., (1980) Am. J. Obstet. Gynecol. 138:1222–1223.
Mainguene et al., (1986) J. Nucl. Med. Allied Sci. 30:19–22.
Miotti et al., (1985) Cancer Res. 45:826–832.
Stall et al., (1981) J. Reprod. Med. 26:73–79.
Tagliabue et al., (1985) Cancer Res. 45:379–384.
Thor et al., (1987) Cancer Res. 47:505–512.
Tsuji et al., (1985) Cancer Res. 45:2358–2362.
Ward et al., (1987) Br. J. Obstet. Gynecol. 94:696–698.
Chow et al., (1985) J. Appl. Biochem. 7:114–121.
Bhattacharya et al. UICC, 14th Int'l. Cancer Congress, Budapest Hungary Aug. 21–25, 1986 vol. 0(0):702 1986.
Goding "Monoclonal Antibodies:Principles and Practice", Academic Press, 1983, pp. 118–124.
Thorpe, in "Monoclonal Antibodies '84: Biological and Clinical Applications", Pinchera et al., Eds., 1985, pp. 475–506.
Milstein in "Handbook of Expt'l. Immunology" vol. 4 Weir et al. Eds., 1986, pp. 107.1–107.12.
Hird et al. in Carney et al. Genes and Cancer, John Wiley & Sons Ltd., 1990, pp. 183–189.
Waldman, Science 252:1657–1661, 1991.
Dillman, Annals Internal Medicine III:592–603, 1989.
Harris et al. Tibtech II:42–44, 1993.
Buchsbaum et al. Med Phys. 20:551–567, 1993.
Vitetta et al., Science 238:1098–1104, 1987.
Casali et al. Science 234:476–479, 1986.

*Primary Examiner*—Paula K. Hutzell
*Attorney, Agent, or Firm*—Morrison & Foerster LLP

[57] ABSTRACT

Monoclonal antibodies immunoreactive with tumor-associated antigen, CA 215 which is present on an ovarian tumor cell line, fragments of those antibodies (either radiolabeled, bound to a toxin, or unlabeled), and the cell line which secretes them are described.

6 Claims, 12 Drawing Sheets

Biochemical and Immunological Properties of selected Monoclonal Antibodies against OC-3-VGH Cells and the Associated Antigens

| Monoclonal Antibodies | Immunoglobulin Subclass | [a]Indirect Immunofluorescent Staining (F/L) | [b]Associated Antigens (Mol. Weight) | [c]Nature of Antigens (S/M) |
|---|---|---|---|---|
| RC 8 | IgG1 | F and L | 25 KD | M |
| RC 26 | IgG1 | F and L | 25 KD | M |
| RC 30 | IgG2 | L | 20 KD | S |
| RC 32 | IgG1 | L | 25 KD | S |
| RC 33 | IgG2 | F and L | ND[d] | S |
| RC 35 | IgG1 | F | 32 KD | S |
| RP 202 | IgG1 | F and L | ND | S |
| RP 215 (HB 10095) | IgG1 | F and L | 60 KD | S |

[a] F: positive staining with methanol-fixed OC-3-VGH cells
L: positive staining with live OC-3-VGH cells

[b] determined by Western Blot Assay

[c] S: soluble antigen
M: membrane-bound antigen

[d] ND: not detected

FIG. 1

Immunoactivity on Monoclonal Antibodies With Normal Human Tissues and Tumor Cells

| Tissues or Cells | Monoclonal Antibodies[d] | | | | | | | | | | |
|---|---|---|---|---|---|---|---|---|---|---|---|
| | RC 8 | RC 26 | RC 30 | RC 32 | RC 33 | RC 35 | RP 215 (HB 10095) | RP 222 |
| OC-3-VGH cells[a] | + | + | + | + | + | + | + | + |
| Heart[b] | – | – | – | – | ± | – | – | – |
| Spleen[b] | – | – | ± | – | – | – | – | ± |
| Kidney[b] | – | – | – | ± | ± | ± | – | – |
| Liver[b] | – | – | – | – | – | – | – | – |
| Testis[b] | – | – | – | ± | – | ± | – | ± |
| Brain[b] | – | – | – | – | – | ± | – | – |
| Muscle[b] | – | – | – | ± | – | – | – | – |
| Ovary[c] | + | + | – | – | – | + | – | + |
| Cervix[c] | + | – | – | – | – | – | – | – |

[a] determined by indirect immunofluorescent assay

[b] determined by immunohistochemical staining method and quantitative tissue adsorption experiments

[c] determined by immunohistochemical staining method

[d] The degree of cross-reactivity to human tissues followed the order of +, ± and –

FIG. 2

MONOCLONAL ANTIBODIES AGAINST AN ANTIGEN ASSOCIATED WITH OVARIAN CERVICAL AND OTHER TUMORS

This application is a continuation, of application Ser. No. 07/388,032, filed 31 Jul. 1989, now abandoned.

DESCRIPTION

1. Technical Field

The invention relates to monoclonal antibodies immunoreactive with a tumor cell marker, and to techniques for diagnosis and treatment of tumors bearing this antigen.

2. Background of the Invention

Early diagnosis of tumors is difficult, mainly because of the lack of reliable and specific tumor markers. Currently available treatments, such as radiotherapy and chemotherapy, are often hampered by their apparent lack of tumor specificity and low therapeutic/toxic ratios.

Ovarian tumors are among the most lethal gynecological cancers. Of the total deaths caused by all gynecological malignancies, nearly half (about 47%) are ovarian cancers. If early detection of ovarian cancers were possible, and followed by proper clinical treatment, the five-year survival rate could climb as high as 76% (Ken, E. et al. (1981) *J. Reprod. Med.* 26:73–79).

Although human chorionic gonadotropin and alpha-fetoprotein could be useful markers for detecting ovarian cancers of germ cell origin, no reliable biochemical markers have been identified for early diagnosis of epithelial ovarian tumors.

Carcinoembryonic antigen was once thought to be a promising marker; however, the positive identification rate of ovarian tumors has remained low. Ken et al. (1981), supra; Donaldson, E. S. et al. (1980) *Cancer* 445:948–953; Accola, R. S. et al. (1980) *Proc. Nat'l Acad. Sci. USA* 77:563–566; Kawahara, M. et al. (1986) *Cancer* 58:2008–2012. The use of heterologous polyclonal antisera against certain types of ovarian tumor extracts or tumor cells, such as OCA, OCAA and NB/70K, are reported. The raised antisera have been used to develop radioimmunoassays or immunohistological assays for the detection of tumor-associated antigens in sera or tissues of cancer patients during early diagnosis and monitoring (Knauf, S. and Urbach, C. I. (1978), *Am. J. Obstet. Gynecol.* 131:780–787; Bara J. et al. (1977), *Br. J. Cancer* 36:49–56; Imamura, N. et al. (1978), *Int. J. Cancer* 21:570–577). This approach is not satisfactory, however, due to the lack of tumor specificity.

With the development of hybridoma technology, it has become possible to generate monoclonal antibodies (Mabs) that are highly specific to single epitopes of antigens, including those associated with tumors. Many investigators have generated Mabs against different ovarian tumors (Accola, R. S., et al. (1980), supra; Kawahara, M., et al. (1986), supra; Knauf, S., and Urbach, G. I. (1980) *Am. J. Obstet. Gynecol.* 138:1222–1223; Kabawat, S. E., et al. (1983) *Am. J. Clin. Pathol.* 79:98–104; Tagliabue, E., et al. (1985) *Cancer Res.* 45:379–384; Tsuji, Y., et al. (1985) *Cancer Res.* 45:2358–2362; Bhattacharya, M., et al. (1982) *Cancer Res.*, 42:1650–1654; Bast, R. C., Jr., et al. (1981) *J. Clin. Invest.* 68:1331—1337; Fleuren, G. J., et al. (1987) *Virchows Archiva* 410:481–486; Mainguene, C., et al. (1986) *J. Nucl. Med. Allied Sci.* 30:19–22; Thor, A., et al. (1987) *Cancer Res.*, 47:505–512; Miotti, S., et al. (1985) *Cancer Res.*, 45:826–832). The most notable and established Mabs are those reactive to CA 125, CA 19-9, HMFG-2 and NB/70K.

Although the Mab specific to CA 125 has been shown to detect related tumor-associated antigens among 80% of patients with nonmucinous ovarian carcinomas (Kabawat et al. (1983), supra), it has limited usefulness in detecting disease since the antigen is also found in normal adult tissues which are derived from coelomic epithelium and other types of tumors (Mainguene et al. (1988), supra; Kabawat, S. E., et al. (1983) *Int. J. Gynecol. Pathol.* 2:275–285; Bast, R. C., Jr., et al. (1983) *N. Engl. J. Med.* 309:883–887). Moreover, CA 125 Mabs are unable to predict the absence of microscopic diseases in patients with complete remission (Attack et al. (1986) *Am. J. Obstet. Gynecol.* 154:287–289; Alvarez, R. D., et al. (1987) *Gynecologic Oncology* 26:284–289). In addition, when using CA 125, the diagnostic positive rate for patients at early stages of cancers was only 18% (Ward, B. G., et al. (1987) *Br. J. Obstet. Gynecol.* 94:696–698). The Mabs CA 19-9, HMFG-2 and NB/70K had similarly low rates of early detection (Kawahara, M., et al. (1986) *Cancer* 58:2008–2012; Ward et al. (1987), supra; Bast, R. C., Jr., et al. (1984) *Am. J. Obstet. Gynecol.* 149:553–559).

The present invention provides monoclonal antibodies that are highly specific to a newly identified tumor associated antigen, designated CA 215. These antibodies have the improvement of not reacting with normal tissues. Thus, the antibodies of the present invention provide a more accurate means of early detection, which is critical to treatment. In addition, serum levels of the CA 215 antigen have been shown to be correlated to disease progression (unlike serum levels of the established ovarian tumor marker, CA 125). Thus, the monoclonal antibodies RP 215 (ATCC Accession No. HB 10095) and the tumor-associated antigen, CA 215, recognized by these antibodies have diagnostic and therapeutic applications for the management of patients with ovarian, cervical and other tumors.

DISCLOSURE OF THE INVENTION

In one aspect, the present invention is directed to monoclonal antibodies that are immunoreactive with a previously unreported tumor-associated antigen, designated CA 215 herein, and fragments thereof which retain antigen specificity such as Fab or F(ab')$_2$ subfragments.

The present invention is also directed to purified forms of the cancer-associated CA 215 antigen, which has an apparent molecular weight of 60 kd on SDS-PAGE gels, and which exists as aggregates of about 100 kd to $1 \times 10^3$ kd in its native state.

Another aspect of the invention is directed to the monoclonal antibodies or subfragments thereof covalently bound to a radioactive label or a toxin.

Still another aspect of the invention is an immortalized cell line which secretes the monoclonal antibodies and which cell line may be a hybridoma.

Still another aspect of the invention is a pharmaceutical composition which comprises monoclonal antibodies immunoreactive with the tumor-associated antigen CA 215 or fragments thereof in admixture with at least one pharmaceutically acceptable excipient.

Still another aspect of the invention is a method to determine the location of tumors bearing the antigen CA 215, which method comprises administering to a subject a labeled monoclonal antibody composition which comprises antibodies immunoreactive with the antigen CA 215, providing a means for detecting the presence of the administered monoclonal antibodies, and detecting the location of the administered monoclonal antibodies.

Still another aspect of the invention is a diagnostic or therapeutic kit which comprises labeled monoclonal antibodies that are immunoreactive with the antigen CA 215 or subfragments thereof.

The following disclosure will render these and other embodiments of the present invention readily apparent to those of skill in the art.

BRIEF DESCRIPTION OF THE DRAWINGS

FIG. 1 is a table which shows biochemical and immunological properties of monoclonal antibodies selected for reactivity with OC-3-VGH cells and the associated antigens.

FIG. 2 is a table which shows immunoreactivity of the monoclonal antibodies of the invention with normal human tissues and tumor tissue cells.

MODES OF CARRYING OUT THE INVENTION

A. Definitions

Figure 3A:
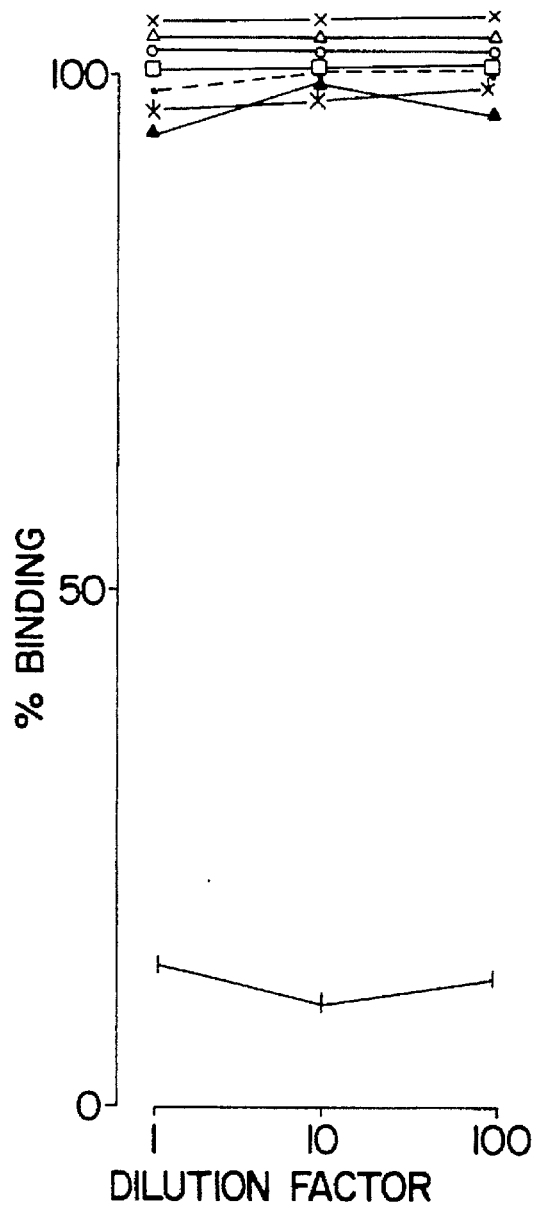
FIG. 3 is a graph which shows determination of tissue-specificity of monoclonal antibodies RP 215 (FIG. 3A) and RP 202 (FIG. 3B) against the ovarian cancer cell line OC-3-VGH (Chao, K. C., et al. (1983) Chin. Med. J. 39:147–152) cells by quantitative tissue adsorption experiments.

Antibodies which are "immunoreactive" with a particular antigen refers to antibodies which have the ability to react positively with the particular antigen to the exclusion of other antigens. It is recognized that at a high enough concentration, immunoglobulins in general will bind to substrates nonspecifically. This nonspecific binding can be discerned, however, by diluting the sample to an appropriate concentration and comparing the effects of this dilution to dilutions of an "immunoreactive" antibody.

"Immortalized cell line" refers to a cell line which can, for practical purposes, be perpetually maintained in cell culture, that is, for an indefinite number of transfers. An immortalized cell line can also be immortalizing so that it is able to confer this property on a fusion product when fused to an ordinary, nontransformed cell line.

The "CA 215" antigen refers to an antigen specifically associated with tumor tissue which binds to the monoclonal antibody HB 10095. The epitope of CA 215 which is recognized by HB 10095 is a peptide moiety and not a carbohydrate moiety. The dissociation constant between the binding of HB 10095 and CA 215 is about $5\times10^{-9}$M. HB 10095 can be used in a Western blot assay to detect the CA 215 antigen. The monomeric form of this antigen shows an apparent molecular weight on SDS-PAGE (or in a purified state) of 60 kd. In its native state, the antigen exists as aggregates of about 100 kd to 2000 kd. The CA 215 aggregates are stable between about pH 4.0 to 9.0 and up to about 70 degrees C. CA 215 behaves as a membrane-associated, soluble protein located on the tumor cell surface.

"Purified form" of the CA 215 antigen means antigen purified from cells which contain the CA 215 antigen. This purification can be done, for example, from the cell extracts or shed medium of such cells using immunoaffinity chromatography using HB 10095 as the affinity ligand. When analyzed by, for example SDS gel electrophoresis, the purified form will be either virtually free of extraneous cellular or media contaminants or will be concentrated at least 250–500 fold more than the original shed medium or cell extract.

"Cross-reactive" means the cross-reactive antibody will inhibit the binding of the reference antibody to antigen at comparable concentrations. Typical assays for cross-reactivity are well known in the art.

"Cells," "cell line," "cell cultures," "recombinant host cells," or "host cells" are generally used interchangeably as will be clear from the context, unless otherwise specified. These terms include but are not limited to individual cells, harvested cells, cultures containing cells, and so forth. Furthermore, a particular designation includes the progeny of that originally prepared. It is understood that spontaneous or induced changes can take place in the DNA and morphology of cells over several generations. Progeny which contain such changes are still included within the definition so long as the progeny retain the essential features of the invention. For example, for a hybridoma which secretes the monoclonal antibody specific against tumor tissue, any descendant of a secreting cell originally identified is included so long-as it continues to secrete the antibody with desired characteristics.

For convenience, clones of immortalized cells and the monoclonal antibodies they secrete will be designated by the same name-for example, the ATCC accession number "HB 10095" refers both to the antibody and to the cells secreting it.

A "pharmaceutical composition" is a pharmaceutically acceptable composition which comprises an active ingredient, such as the monoclonal antibodies of the present invention and, if desired, a carrier suitable for the required formulation. If the pharmaceutical composition is formulated as a solid composition, conventional nontoxic solid carriers which may be used include, for example, pharmaceutical grades of mannitol, lactose, starch, magnesium stearate, sodium saccharin, talcum, cellulose, glucose, sucrose, magnesium carbonate and the like. The pharmaceutical composition, as defined above, may be formulated as suppositories using, for example, polyalkylene glycols (propylene glycol, for example) as the carrier. Pharmaceutical compositions may, for example, be formulated as an administrable liquid by dissolving, dispersing, etc. an active ingredient and optional pharmaceutical adjuvants in a carrier, such as, for example, water, saline, aqueous dextrose, gylcerol, ethanol, and the like, to form a solution or suspension. If desired, the pharmaceutical composition to be administered may also contain minor amounts of nontoxic auxiliary substances, such as wetting or emulsifying agents, pH buffering agents and the like, which include for example, sodium acetate, sorbitan monolaurate, triethanolamine sodium acetate, triethanolamine oleate, etc. Actual methods of preparing such dosage forms are known, or will be apparent, to those skilled in this art; see, e.g., *Remington's Pharmaceutical Sciences*, Mack Publishing Company, Easton, Pennsylvania, 17th Edition, 1985. The composition or formulation to be administered will, in any event, contain a quantity of the active compound(s) in an amount effective to alleviate the symptoms of the subject being treated.

If the liquid pharmaceutical composition is to be used for parenteral administration, administration will generally be characterized by injection subcutaneously, intramuscularly, or intravenously. Injectable compositions can be prepared in conventional forms as liquid solutions or as suspensions, in solid forms which are suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of nontoxic auxiliary substances such as wetting or emulsifying agents, pH buffering agents, and the like, such as, for example, sodium acetate, sorbitan monolaurate, triethanolamine oleate, etc.

B. General Method

Disclosed below are procedures for preparation of monoclonal antibodies immunoreactive with the tumor-associated antigen, CA 215, procedures for labeling these, antibodies, and for using these labeled antibodies either to locate tumors or to treat patients with CA 215-bearing tumors. Also described are procedures for biochemical and immunological characterization of selected monoclonal antibodies. In general, the procedure of Kohler and Milstein is adapted to the preparation of the desired antibodies and, if desired, followed by obtaining appropriate switch variants using the method of Dangl, J. L., and Herzenberg, L. A. (1982) *J. Immunol. Meth.* 52:1.

Hybridomas capable of secreting the desired monoclonal antibodies are created by fusing spleen cells, or peripheral blood lymphocytes from a mammal immunized with ovarian cancer cells, to cells of an immortalizing cell line: typically a myeloma line of the same species as that from which the antibody-secreting cell is derived. Convenient myeloma lines are available from mouse and rat; these mammals therefore make good subjects for production of polyclonal antisera and the immunoglobulin-secreting cells. However, it is understood that any available immortalizing cell line may be used with secreting cells obtained from a compatible species. In addition, certain antibody-secreting cells may be immortalized by viral infection, such as by treating with Epstein-Barr virus. These alternate immortalizing techniques may also be employed to obtain the immortalized immunoglobulin-secreting cells of the invention.

Hybridomas are created by fusing the antibody-secreting cell line with the immortalizing cell line in the presence of an activating agent such as polyethylene glycol. Details of this, now standard, procedure are known in the art and need not be recited here. The critical parameters determining success or failure generally relate to the choice of immortalizing cell lines or method of immortalizing, and to the choice of the population of antibody-producing cells. This latter preparation is, in turn, dependent on the use of the correct immunizing agent for administration to the mammal generating these cells.

Figure 5:
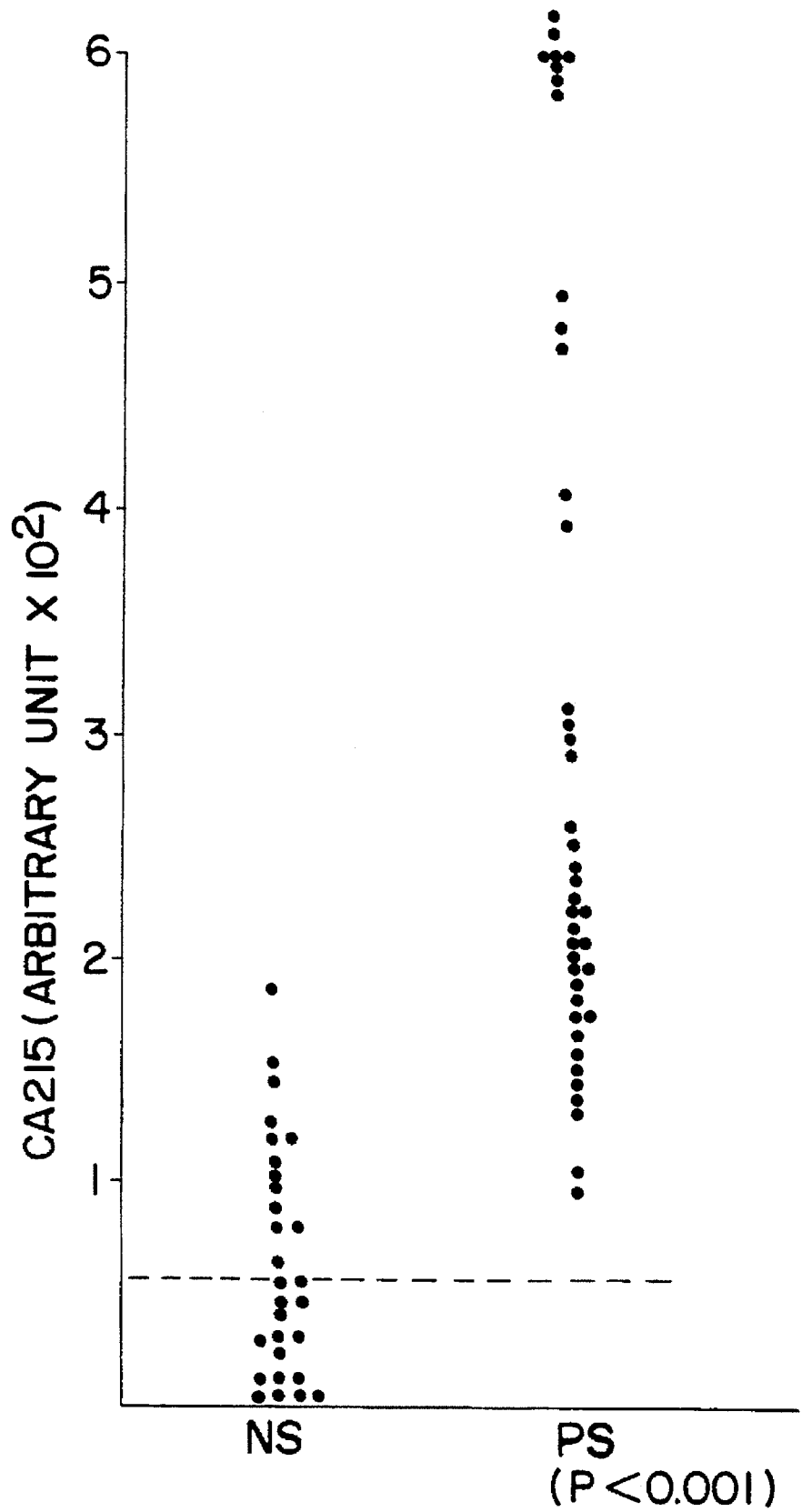
FIG. 5 is a chart which shows determination of serum CA 215 levels of patients with ovarian cancers and those of normal healthy women.

The mammal may, for example, be immunized with the purified CA 215 antigen rather than the broad spectrum of tumor proteins. Purified CA 215 antigen may be obtained by sonicating tumor cells and centrifuging the lysate in low salt buffer to obtain the soluble membrane fraction; loading the supernatant on a gel filtration column, such as Sephacryl S-300; and collecting fractions to be assayed for the amount of antigen. As another alternative, the antigen can be purified from the ascites fluid of a mammal immunized with whole tumor cells by performing ammonium sulfate fractionation followed by DEAE ion exchange chromatography, collection of fractions, and assayed. The fractions containing antigen may be detected by a number of means. For example, aliquots of the individual fractions can be electrophoresed on polyacrylamide gels and the fraction containing the antigen (minimum molecular weight of 60 kd and also existing in its native state as aggregates of 100 kd–2000 kd) thereby determined by comparison either to standard molecular weight markers or, if available, a sample of the antigen itself. (An elution profile of this antigen from a gel filtration column is shown in FIG. 5.)

In a preferred hybridoma preparation procedure, isolated spleen cells from the immunized mice are fused with a myeloma line derived from the same species, such as NS-1 myeloma cells using 50% PEG, and the resulting cells grown on selective media. Many readily available myeloma lines are HAT- or AH-sensitive, that is, they fail to grow in either HAT medium, which contains hypoxanthine, aminopterin, and thymidine, or in AH medium, which contains azaserine and hypoxanthine. Both of these media take advantage of the capacity of normal cells to utilize a salvage pathway for DNA synthesis under circumstances where the de novo process is inhibited (in this case, by aminopterin or azaserine). Hypoxanthine and thymidine (or hypoxanthine alone) are requirements for the salvage pathway.

Therefore, only immortalizing cells which are fused to normal cells are capable of survival in this selection medium; unfused immortalizing cells, which are HAT- or AH-sensitive, will die. (Normal cells which have not been immortalized by fusion would, of course, eventually die anyway.) Only cultures containing fused cells are ultimately available for screening to detect production of the desired antibody.

Cultures of fused cells which survive in selection medium or cells immortalized by other methods are then screened for secretion of antibody having the desired characteristics. A number of screening methods are useful for identifying antibodies to the CA 215 antigen. For example, the culture media may be assayed using immunoreaction-based assays, including, without limitation, Western blot, ELISA, and radioimmunoassay (RIA).

The antigen used for this screen must be chosen to insure the correct specificity. Useful in this regard are the cell lines such as human ovarian, cervical or other tumor cells (as, for example, the human ovarian cell line OC-3-VGH) or those of other species which are suitably cross-reactive. Particularly desirable is screening with the herein identified CA 215 tumor characteristic antigen of molecular weight 60 kd (on SDS-PAGE gels) and existing in its native state as aggregates with molecular weights ranging from 100 kd to 2000 kd (See, e.g., FIG. 1 and FIG. 12).

The preferred monoclonal antibodies will have particular features. For example, the Mab will also be cross-reactive with HB 10095. The Mab will react with highest specificity to tumor cells, such as the OC-3-VGH ovarian tumor cell line, and have no significant cross-reactivity with normal human tissues, as shown, for example, by quantitative tissue adsorption or PAP (peroxidase anti-peroxidase) staining. The Mab will be capable of reacting, for example, using indirect immunofluorescence assay, with both live and fixed tumor cells. (See, e.g., FIG. 1). The assay will also include negative screens to insure tumor specificity.

Once a line has been identified as secreting the correct antibodies, the antibodies can be recovered from the medium using standard purification techniques. In addition, standard techniques are also available for labeling the antibodies so isolated.

The Mabs of the present invention may be used in immunoassays, which may be marketed commercially in kit form. Immunoassay kits employing the Mabs of the present invention may be used to diagnose the presence of ovarian, cervical, and other tumors bearing the CA 215 antigen. The labeled antibody reagent (i.e., radiolabeled or as an immunotoxin conjugate) may be packaged in unit dosage form, including means for administration, such as an injection syringe, if desired. The ability of the Mabs of the present invention to detect levels of tumor-associated antigen in sera make such assays especially useful for early diagnoses.

Methods to conduct immunoassays are known in the art, and there are numerous protocols available. Examples of several suitable prototype protocols are provided below in the description of the screening assays used for detecting the antibodies of the invention.

The Mabs of the present invention may also be conjugated to radiolabels for tumor imaging.

Use of Labeled Monoclonal Antibodies in Imaging

Labeled monoclonal preparations are useful in locating tumor tissue in patients undergoing surgery. Techniques for labeling antibodies or their subfragments are well known in the art, and a variety of labels are used, depending on the purposes for which the immunoglobulins are intended, including fluorescent, chromogenic, and radioactive labels. Typically, for in vivo applications radiolabeled antibodies are preferred, as this permits detection of the internalized antibodies.

A number of radioisotopes are commonly used, including iodine-123, iodine-125, iodine-131, technetium-99, gallium-67, and indium-111. Technetium-99 has a half-life of approximately six hours, which may be too short for some purposes or it may require use of levels of radiation which are higher than desired. Indium-111, on the other hand, appears to be a preferred isotope, since it has a half life of three days.

Methods for binding these isotopes to the antibody or a fragment of antibody are understood in the art and include the use of iodination with 1,3,4,6-tetrachloro-3a,6a-diphenylglycocuril (Fraker, P. J., et al. (1978) *Biochem. Biophys. Res. Comm.* 80:849–857) and the covalent coupling of a chelating agent capable of binding metal ions such as Indium-111, as described by Hnatowich, D. J., et al. (1983) *Science* 220:613–615, which refer to still other approaches to labeling proteins. Other iodinating and chelating methods can be used to attach the foregoing isotopes to the antibody or fragment thereof.

The labeled monoclonal preparation is administered to the patient intravenously in an appropriate carrier at a time several hours to four days before the tissue is to be imaged. During this period, unbound fractions are cleared from the body, and the only remaining labeled monoclonal antibodies are those associated with the tumor tissue. At this time, the subject is placed in front of a suitable gamma camera to detect the presence of the isotope. This results in a "picture" of the labeled tissue, which can be correlated with known markers on the patient's body to pinpoint the location of the tumor for the surgeon.

Use of Monoclonal Antibodies in Treating Patients with CA 215-Bearing Tumors

The high specificity and affinity of the Mabs to the tumor cells also renders the Mabs of the present invention useful for treatment of cancer. For example, these antibodies, as well as antigen-specific fragments of these antibodies, may be conjugated to toxic moieties. These moieties can include, for example, ricin A, diphtheria toxin, abrin, modeccin or bacterial toxins from Pseudomonas or Shigella. Toxins and their derivatives have been reported in the literature to form conjugates with antibodies specific to particular target tissues, such as cancer or tumor cells, in order to obtain specifically targeted cellular toxicity. See, e.g., Moolten, F. L., et al. (1982) *Immun. Rev.* 62:47–72 and Bernhard, M. I. (1983) *Cancer Res.* 43:4420. In addition, certain subclasses such as IgG2a and IgG2b are relatively cytotoxic per se.

Conjugation of the toxic and CA 215-specific moieties can be conducted by standard means known in the art. A number of commercially available bifunctional linking agents are available, for example, from Pierce Chemical company, Rockford, Ill. Such crosslinking agents include, most prominently, heterobifunctional linkers such as N-succinimidyl-3-(2-pyridyldithio)propionate (SPDP) which generate a disulfide linkage at one terminus and an amide linkage with an available amino group on the subject molecule at the other. A number of maleimido containing compounds are also available; these generate thioethers with available sulfhydryls on the subject molecule, along with an amide at the other terminus, for example, succinimidyl-4-(N-maleimidomethyl)cyclo-hexane-1-carboxylate (SMCC). A large number of homobifunctional and heterobifunctional linkers are available and methods for their use are understood in the art.

Administration of the antibodies or immunotoxins for therapeutic use is most conveniently by an intravenous route, although by proper formulation, additional routes of administration such as intraperitoneal, oral, or transdermal administration may also be used. Methods of formulating compositions for administration to human subjects by an appropriate, selected mode of administration are well understood in the art. For parenteral administration, injectables can be prepared in conventional forms as liquid solutions or suspensions or in solid forms suitable for solution or resuspension prior to injection, or as emulsions. Suitable excipients include, for example, water, saline, dextrose, glycerol, ethanol, Hank's solution, Ringer's solution and the like. For administration by suppository, traditional binders and carriers include, for example, polyalkylene glycols or triglycerides and the like.

Dosage levels of the immunotoxins is dependent on the toxicity of the conjugated toxin but will generally be in the range of 0.1–1 mg/kg. The immunotoxin will generally be formulated into vehicles for parenteral administration, such as Hank's solution or Ringer's solution in concentrations of about 1 mg/ml to 10 mg/ml to permit the injection of relatively small volumes.

If antigen-specific fragments are desired for use in radio-imaging or immunotoxin preparations, the Fab or F(ab')$_2$ fragments may be prepared by standard methods, such as those described by Weir, D. M., *Handbook of Experimental Immunology* (3d ed., 1978) Blackwell Science Publ., Oxford.

C. Examples

As a general overview, the monoclonal antibodies of the present invention were generated against an ovarian tumor cell line OC-3-VGH using the above-described hybridoma technology. Of the 3,000 hybrid clones generated, 8 were shown to secrete antibodies with relatively high specificity and affinity to ovarian cancer cells and a low cross-reactivity to most normal human tissues when analyzed by quantitative tissue adsorption experiments and by immunohistochemical staining to analyze for tissue specificity. RP 215 (ATCC Accession No. HB 10095), one of the selected monoclonal antibodies, reacts specifically with the tumor-associated antigen, CA 215. CA 215 has a molecular weight of 60 kd on SDS-PAGE gels and exists as a 100–2000 kd aggregate in its native state. CA 215 was detected in the shed medium of cultured OC-3-VGH cells. The same shedding was detected for antigens reactive to other selected monoclonal antibodies, namely RC 30 and RC 33.

Although CA 215 was originally identified as a tumor-associated antigen from the ovarian tumor cell line OC-3-VGH through the generation of HB 10095, this tumor-associated antigen does not appear to discriminate between patients with ovarian tumors and those with cervical, and probably other, carcinomas. HB 10095 was able to determine with high predictability the antigen levels in sera among ovarian cancer and cervical carcinoma patients. Thus, the selected monoclonal antibodies of the present invention is useful during clinical diagnosis, monitoring, and treatment of patients with ovarian, cervical and other CA 215-bearing tumors.

Described below are examples of the present invention. These examples are provided only for illustrative purposes and are not intended to limit the scope of the present invention in any way. In light of the present disclosure, numerous embodiments within the scope of the claims will be apparent to those of ordinary skill in the art. The contents of the references cited in the specification are incorporated by reference herein.

Materials

The materials used in the following procedures were as follows. The following chemicals were purchased from Sigma Chemical Company, St. Louis, Mo.: dimethylsulfoxide (DMSO), lipopolysaccharide (LPS), methylcellulose, bovine serum albumin (BSA), complete and incomplete Freund's adjuvant, pristane and o-phenylene diamine. Cell culture media including IMDM, RPMI 1640, penicillin-streptomycin (100x) and glutamine were from GIBCO, Burlington, Ontario, Canada. Tissue culture plates and selection media including HAT (hypoxanthine, aminopterine and thymidine, 100x) and HT (hypoxanthine and thymidine, 100x stock) were from Flow Laboratories, Mississauga, Ontario, Canada. Fluorescein isothiocyanate (FITC)-labeled goat antimouse IgG+M+A was from Capple/Worthington, Malvern, Pa.. All the analytical grade reagents required for sodium dodecylsulfate (SDS) acrylamide gel electrophoresis and Western blot assay were from BioRad Laboratories, Richmond, Calif. Polyethylene glycol (PEG, mol. wt. 1500) was from British Drug House Chemicals LTD. Iodine-125 radioisotope was purchased from Amersham, Buckinghamshire, UK.

EXAMPLE 1

Production of Monoclonal Antibodies

In vitro cultured tumor cells derived from an ovarian tumor cell line of serous origin, OC-3-VGH (Chao, K. C., et al. (1983) *Chin. Med. J.* 39:147–152), were used as immunogens. BALB/c mice were used for immunization, cell fusions, and production of monoclonal antibodies using ascites fluid. For immunization, about 1×10$^6$ OC-3-VGH cells in 100 ul phosphate-buffered saline (PBS) were emulsified with an equal volume of complete Freund's adjuvant. The mixture was injected into each mouse subcutaneously. Two more injections were given two and four weeks after the primary immunization, except that incomplete Freund's adjuvant was used. One week after the third injection after immunization, the antisera titers of immunized mice were determined by indirect immunofluorescent assay and enzyme-linked immunosorbent assay (ELISA). (Described infra.) Those immunized mice with the highest titers were injected through the tail vein with 1×10$^6$ tumor cells in 200 ul PBS.

Hybrid cells were initially cultured in a semisolid medium which contained methylcellulose. See Davis et al. (1982) *J. Immunol. Meth.* 50:161–171. Seven to ten days after the cell fusion, three successful experiments produced about 3,000 hybrid clones. The colonies were removed from the semisolid medium and cultured in RPMI 1640 containing 10% fetal calf serum in 96-well microtiter plates.

Cell culture supernatant was screened for the presence of antibodies against OC-3-VGH cells by both ELISA and indirect immunofluorescent assay using methanol-fixed and live cells (described infra). The hybrid cell lines which secreted antibodies of high affinity and specificity were subcultured until they reached a cell density of 1×10$^6$/ml. About 30 hybrid clones were finally selected and were shown to secrete antibodies reactive to OC-3-VGH cells. The hybrid cells were frozen and stored in a liquid nitrogen tank. Mass production of selected monoclonal antibodies was achieved by inducing ascites fluid from BALB/c mice primed with pristane according to standard procedures.

By using the method of Ouchterlony (1958) *Prog. Allergy* 5:1–78, for double immunodiffusion in gel, the immunoglobulin subclasses of these antibodies were determined to be either IgG1 or IgG2. The biochemical and immunological properties of selected monoclonal antibodies are summarized in FIG. 1.

EXAMPLE 2

Biochemical and Immunological Characterization of Monoclonal Antibodies of the Invention 1. Indirect Immunofluorescent Assay.

Indirect immunofluorescent assay was performed using methanol-fixed tumor cells according to the method of Bast et al. (1984), supra. Due to the fact that methanol-fixed cells or paraffin-embedded tissue sections sometimes do not preserve the surface antigens which react with monoclonal antibodies, indirect immunofluorescent assays using live cell suspension were also performed.

Following sonication and centrifugation in low salt buffer, OC-3-VGH cells were first separated into soluble and membrane fractions. They were incubated separately with the selected monoclonal antibodies. 50 ul of cell culture supernatant containing monoclonal antibodies and 50 ul of a suspension of cultured OC-3-VGH cells ($1\times10^5$ cells/ml) were mixed in either microfuge tubes or in microtiter wells. The mixture was incubated at room temperature (rt) for 3 hours. After washing with PBS-BSA and centrifugation, FITC-labeled goat antimouse IgG+M+A was added to the cell suspension and the mixture was incubated for an additional 2 hours. Following 3 washes with PBS-BSA and centrifugation, the final supernatant was discarded. Finally, 10 ul of 80% glycerol in PBS was added to the cell pellet and pipetted on slides for observation under a fluorescence microscope.

The results of this assay revealed that RC 30, RC 32, RC 33, RC 35, RP 215 (HB 10095) and RP 202 react predominantly with the membrane-associated soluble proteins on the surface of OC-3-VGH cells; RC 8 and RC 26 react with the membrane-bound proteins of OC-3-VGH cells as indicated in FIG. 1.

2. Enzyme-Linked Immunosorbent Assay (ELISA)

The specific binding of monoclonal antibodies to OC-3-VGH cells was also determined by ELISA according to the method of Lee, C. Y. G., et al. (1984) *Am. J. Reprod. Immunol.* 6:27–33.

Cells from the OC-3-VGH cell line were cultured in each of 96 wells of microtiter plates until a monolayer was formed. After removal of the culture supernatant, the cell-coated wells were blocked by incubation with PBS-BSA (0.5% BSA in PBS) for 1 hour prior to use in ELISA. After 1 hour of incubation with the test antibody in culture supernatant, wells were washed 3 times with PBS-BSA. Goat antimouse IgG+M+A conjugated with horseradish peroxidase was added to each well for an additional 1 hour incubation period at rt. The wells were washed 3 times with PBS-BSA. o-phenylene diamine (0.2 mg/ml), and 0.02% H2O2 in citrate-phosphate buffer (0.1M) were added to initiate the room temperature enzymatic reaction. After 15 minutes, 1M $H_2SO_4$ was added to stop the color reaction. The color intensity in each well was determined spectrophotometrically at 492 nm by a CLS microplate reader (Cambridge, UK). Normal mouse serum in RPMI medium served as the negative control in all assays. Mouse anti-OC-3-VGH cells antisera served as the positive control.

3. Immunohistochemical Study of Tissue Sections

Formalin-fixed, paraffin-embedded normal human tissue sections were used to determine the specificity or cross reactivity of the generated monoclonal antibodies to various tissues including brain, liver, heart, kidney, spleen, ovary, testis, cervix and muscle. These tissues were obtained at the time of surgery or at autopsy. Paraffin tissue sections were deparaffinized in xylene and then subsequently dipped in 95%, 75% and 50% ethanol and washed with PBS. Cryostat tissue sections were also prepared and dipped in 95% ethanol followed by a wash with PBS. Peroxidase-antiperoxidase (PAP) immunohistochemical staining method was performed according to the reported procedures of Sternberger, L. A., et al. (1982) *Ana. Biochem.* 123:14–22; and Hsu, S. M., et al. (1981) *J. Histochem. Cytochem.* 29:577.

The results of PAP staining of normal human tissue sections revealed that, among these antibodies, 8 were shown to have sufficiently high specificity to OC-3-VGH cells and did not crossreact with other normal human tissues. They are listed in FIG. 2.

4. Radioimmunosorbent Inhibition Assay

Immunohistochemical staining method using peroxidase-antiperoxidase complex was used initially to examine the reactivity of generated monoclonal antibodies to various normal human tissues. The presence of specific antigens in the tissue homogenate which react with the selected monoclonal antibodies was further evaluated by quantitative tissue adsorption experiments using radioimmunosorbent inhibition assay. Briefly, cultured OC-3-VGH cells ($1\times10^6$ cells/ml) were first sonicated and coated on microtiter wells according to the Lee et al. (1984), supra. Monoclonal antibodies of different dilutions in culture supernatant were first incubated with an equal volume of various tissue homogenates (30 mg/ml) either for 2 hours at rt or overnight at 4° C. Following centrifugation to remove any insoluble proteins, the clear supernatant was added to each microwell coated with cultured OC-3-VGH cells and incubated for 2 hours at rt. Following 3 washes with PBS-BSA, $^{125}$I-labeled goat antimouse IgG+M (specific activity 0.1 mCi/ug), which served as the second antibody, was added to each well for an additional 2 hour incubation at 37° C. After 3 washes with PBS-BSA to remove unbound radioactivity, the remaining radioactivity in each well was determined by an LKB minigamma counter. In each experiment, sonicated OC-3-VGH cells of known concentration served as the positive control, whereas PBS, containing 30 mg/ml BSA, served as the negative control. If a given tissue homogenate contains crossreacting antigens to CA 215 which react with the antibody, the binding of the antibody to tumor cell-coated wells will be inhibited in a dose-dependent manner as indicated by this experiment. The inhibition assay can also be performed with ELISA. Goat antimouse IgG+M conjugated with horseradish peroxidase served as the second antibody. The remaining steps of the assay are the same as those described in the previous section. (See section 2, supra.)

Figure 3B:
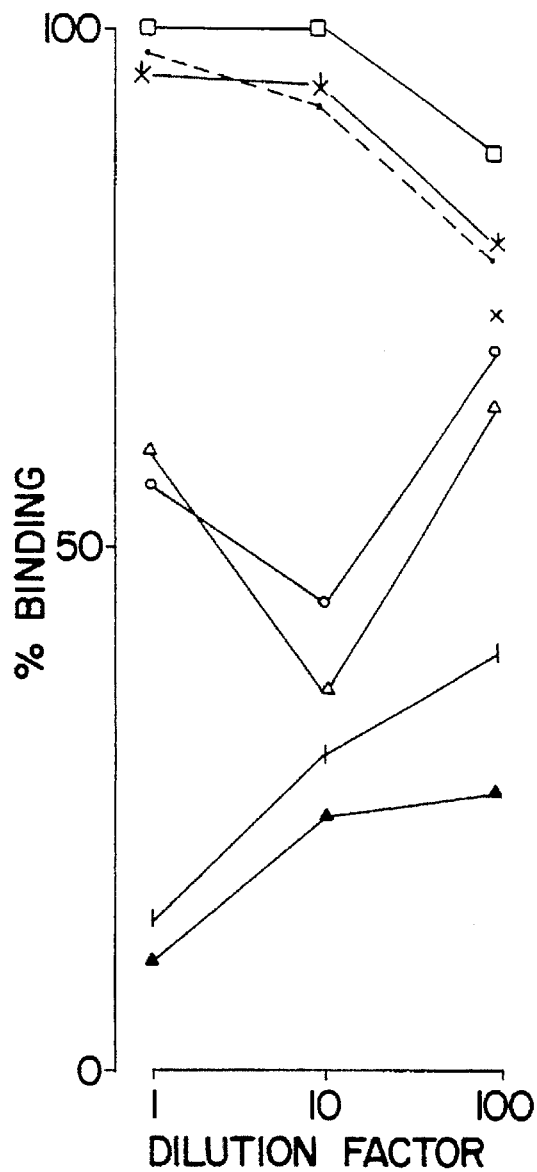

The results of radioimmunosorbent inhibition assay are shown in FIG. 3 in which the percent of maximum binding of antibody to OC-3-VGH cell coated wells (in the presence of PBS-BSA only) is plotted against different antibody dilutions. In FIG. 3, "A" is the RP 215 (HB 10095) antibody and "B" is the RP 202 antibody. HB 10095 is shown to have a higher specificity to OC-3-VGH cells and no significant immunoreactivity with other normal tissues compared to RP 202, which shows some immunoreactivity with some normal tissues.

5. Detection of Shed Antigens from Spent Culture Medium

OC-3-VGH tumor cells were cultured in an RPMI 1640 medium which contained 10% calf serum. When monolayers became confluent in the tissue culture flask, the cells were cultured without changing the medium for an additional 4 days. The supernatant was centrifuged at 27,000×g for 30 minutes to remove any cell debris and membrane fragments. The clear supernatant was then passed through Millipore filters and concentrated fivefold by dialysis in PEG powder hallowed by extensive dialysis against PBS. The amount of various antigens in the spent medium was determined by radioimmunosorbent inhibition assay. (See section 4, supra.)

The presence of specific antigens in the spent medium was detected by the inhibition of the binding of selected monoclonal antibodies to the OC-3-VGH cells which had been coated on microwells. The binding of antibodies to coated tumor cells was determined by incubating, in complete RPMI medium for 1 hour at rt, a constant amount of concentrated spent medium with different dilutions of the antibody. This was followed by 3 washes with PBS-BSA and incubation with 0.1 uCi/well of $^{125}$I-labeled goat antimouse IgG+M in RPMI medium at rt for an additional 2 hours. At the end of the incubation, the microwells were washed 3 times with PBS-BSA and counted for residual activity by an LKB minigamma counter. RPMI medium containing 50% calf serum served as the negative control. Goat antimouse IgG+M was labeled with I (0.1 mCi/ug) according to the chloramine T method of Greenwood, F. C., and Hunter, W. N. (1963) *Biochem. J.* 80:114–123.

Figure 4:
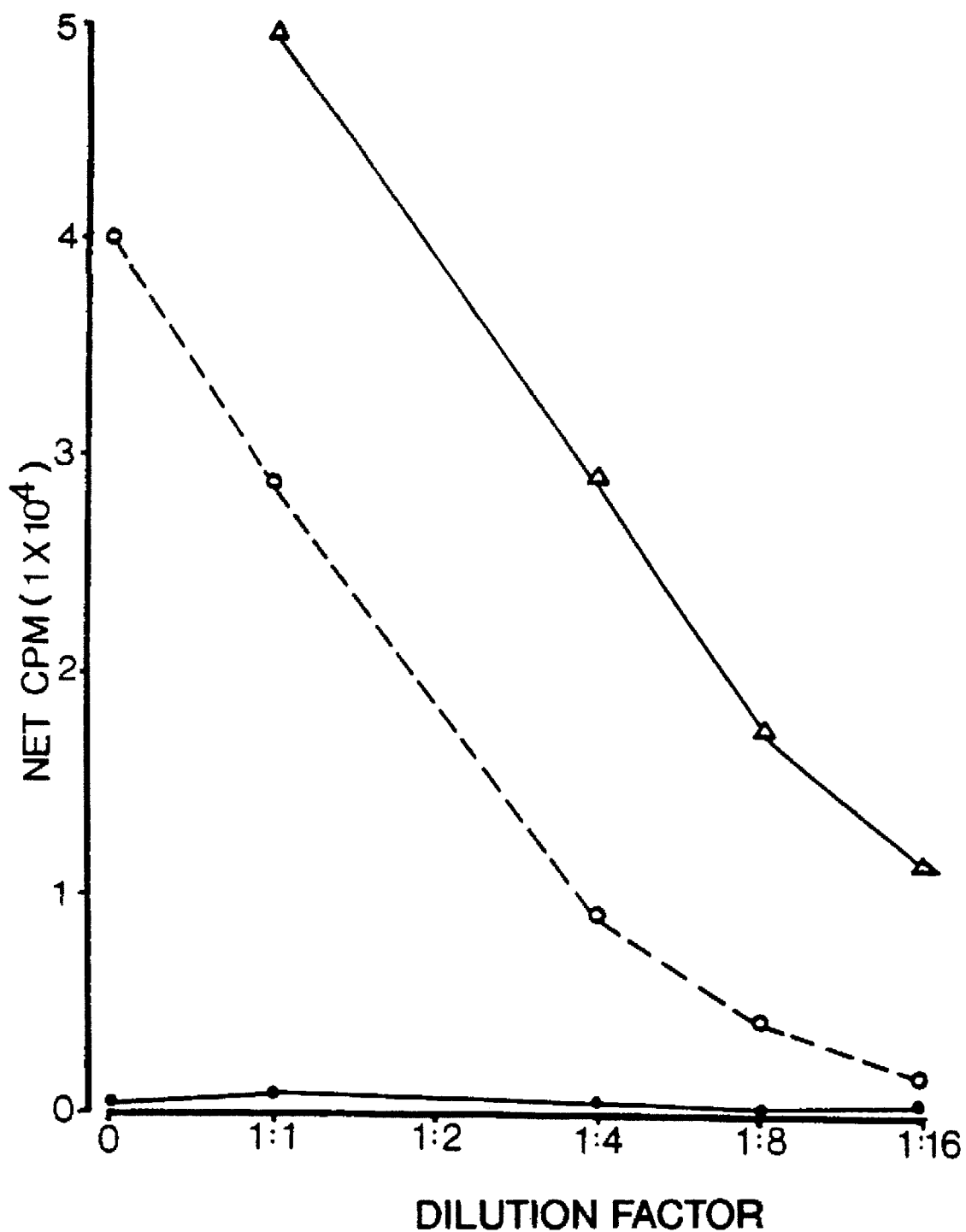
FIG. 4 is a chart which shows detection of shed antigens reactive to the RP 215 monoclonal antibody (ATCC Accession No. HB 10095) in the spent medium of cultured OC-3-VGH cells by radioimmunoadsorbent assay.

As shown in FIG. 4, the specific antigen that is present in the spent medium appeared to inhibit the binding of HB 10095 (RP 215) monoclonal antibody to tumor cells. Similarly, the binding of RC 30, RC 33, and RC 35 to the tumor cell surface was also significantly reduced by the presence of shed antigens in the concentrated spent medium. In contrast, no significant inhibition was observed for the binding of RC 8, RC 26, and RC 32 to the coated tumor cells by the added spent medium.

EXAMPLE 3

Determination of Carcinoma in Patients

HB 10095 was used in a sandwich immunoradiometric assay procedure was used to compare serum levels of CA 215 in healthy women with subjects having ovarian carcinomas, cervical carcinomas, endometriosis, and pelvic benign tumors at different disease and treatment stages. HB 10095 was purified from ascites fluid by ammonium sulfate fractionations and DEAE ion exchange chromatography according to Chow, S. N., et al. (1985) *J. Appl. Biochem.* 7:114–121. Purified monoclonal antibody was coated to microwells at a concentration of 5 ug/ml in Tris-HCl, pH 8.0. At the same time, it was labeled with $^{125}$I with a specific activity of 0.1 mCi/ug using a Chloramine T method; this served as the second antibody tracer in the sandwich assay.

The immunoassay was initiated by incubating 100 ul each of human serum and $^{125}$I-labeled HB 10095 in antibody-coated microwells for 2 hours at rt. After incubation the content of microwells was removed by suction. The wells were washed 3 times with PBS-BSA and counted for residual radioactivity by an LKB minigamma counter. PBS containing 50 mg/ml BSA served as the negative control. Supernatant of cultured OC-3-VGH cells served as the positive control for the assay of CA 215.

The results of this analysis are presented in FIG. 5 and compared with those of normal healthy women. In FIG. 5, "NS" refers to serum of normal healthy women (n=29) and "PS" refers to serum of patients with ovarian tumors (n=31). In terms of the arbitrary units, under identical assay conditions, CA 215 levels for the normal healthy individuals ranged from 0 to 180 U/ml, whereas those in ovarian tumor patients ranged from 101 to about 1,000 U/ml. There is a clear statistical difference in terms of the serum CA 215 levels between the cancer patients and the normal individuals.

Figure 6:
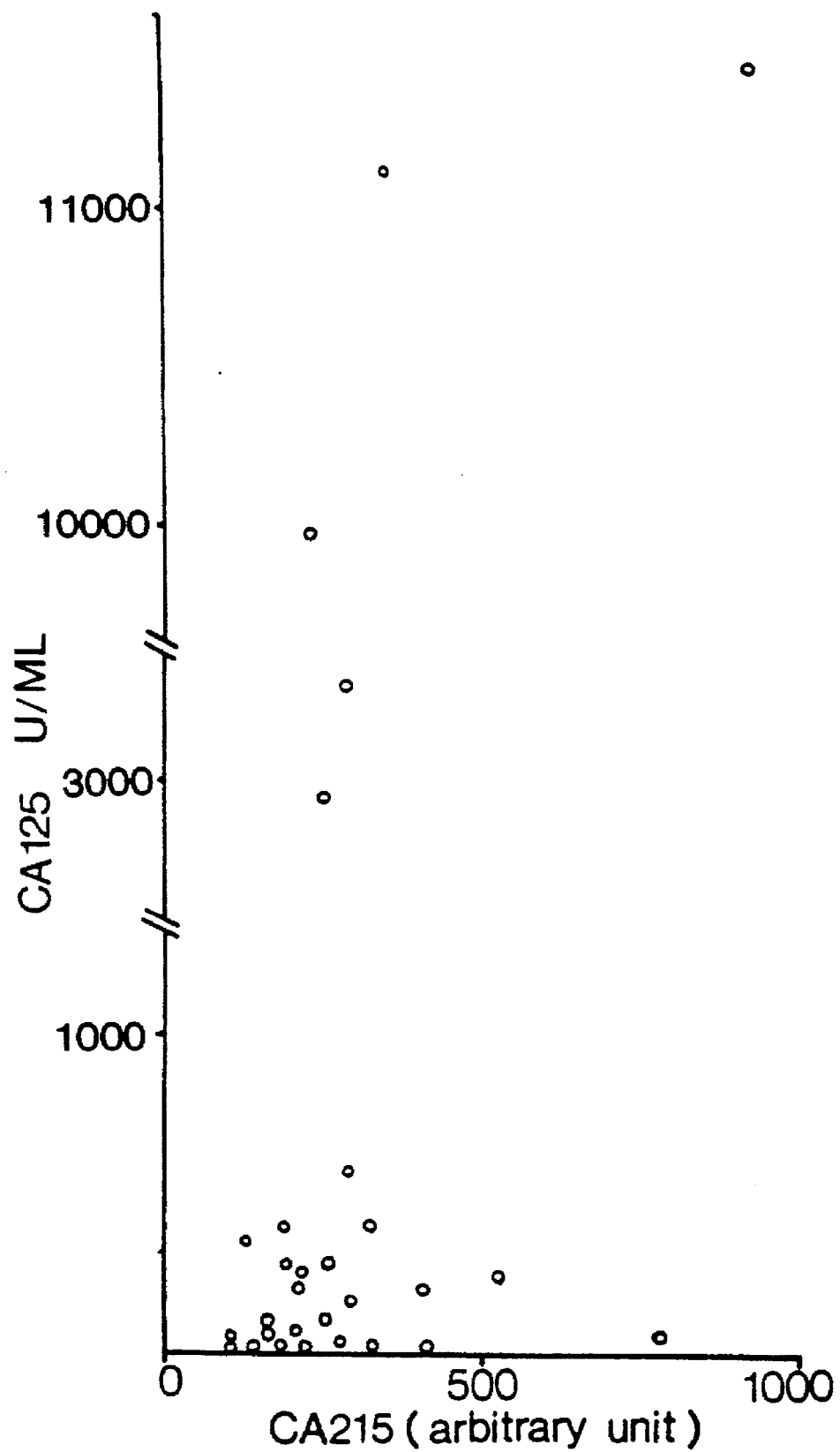
FIG. 6 is a chart which shows a correlation analysis of serum levels of CA 125 and CA 215 for ovarian cancer patients.

In order to compare the specificity and sensitivity of CA 215 and the known CA 125 in terms of diagnosis of ovarian cancers, serum levels of CA 125 were also determined for the same group of ovarian cancer patients using a commercially available radioimmunoassay kit (Centocor, Malvern, Pa.). Parallel determinations of serum CA 125 and CA 215 were performed. It was discovered that the majority of the ovarian cancer patients showed significantly elevated levels of CA 215 as compared to those of normal, healthy individuals. It was also discovered that there is no apparent correlation between the serum levels of CA 215 and those of CA 125 to a given serum specimen from ovarian cancer patients, as shown in FIG. 6.

These results clearly indicate that serum levels of CA 215 among ovarian cancer patients are significantly higher than serum levels of CA 215 in normal individuals. Furthermore, for any given ovarian cancer patient, serum CA 215 levels are not correlated with that of the established ovarian tumor marker, CA 125.

In a second study, HB 10095 was used to compare CA 215 levels in sera of healthy subjects to sera CA 215 levels of patients with both ovarian and cervical carcinomas, as well as endometriosis and pelvic benign tumors, all at different disease stages and conditions.

In this study, HB 10095 was labeled with $^{125}$I (with a specific activity of 10 ug/mCi) and used as the second antibody for the assay. One hundred ul of each serum sample and 100 ul of $^{125}$I-labeled HB 10095 (1×10$^6$ cpm/well) were added to each microwell, and allowed to incubate at 4° C. for 18 hr. Following incubation, the contents of the microwells was removed by suction. The wells were then washed 5x with PBS-Tween (Tween-20, 0.02%), and residual radioactivity in each microwell was determined by an LKB Minigamma Counter. The sonicated extract of OC-3-VGH cells was used as positive control for all the assays. CA 215 concentration in a sonicated OC-3-VGH cell supernatant, containing 1 absorbance unit at 280 nm/ml was arbitrarily designated to be 100 U/ml. The dose-dependent curve of the sandwich assay was shown to be linear up to 100 u/ml of CA 215 in serum or in the positive control.

Figure 7:
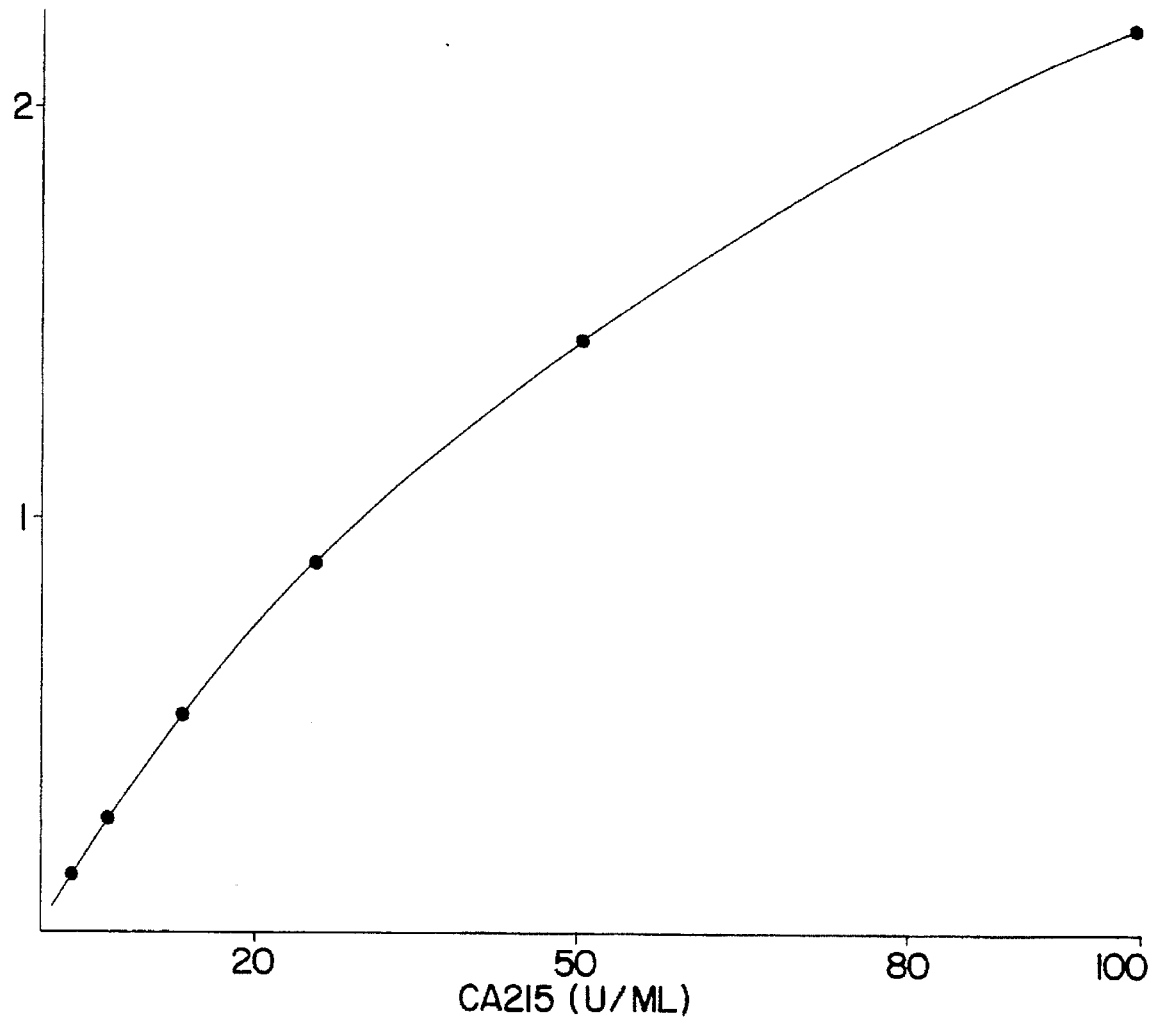
FIG. 7 is a graph which shows a standard curve of an immunoradiometric assay for the determination of CA 215 concentration using the supernatant of OC-3-VGH cell extract in which a concentration unit of 100 u/ml was assigned to supernatant having 1 absorbance unit at 280 nm/ml.
Figure 8:
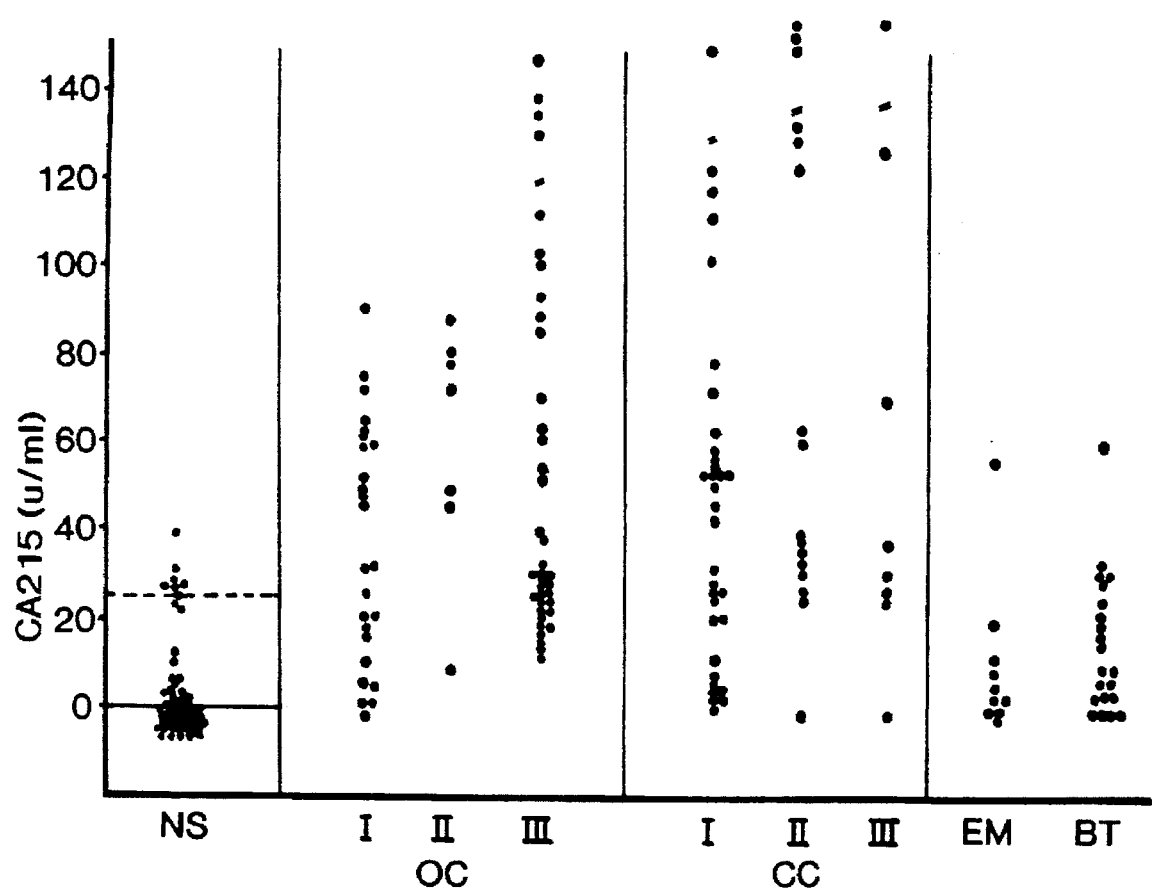
FIG. 8 is a chart which shows serum levels of CA 215 for normal individuals (NS); for patients with ovarian carcinoma (OC) and cervical carcinoma (CC), both carcinomas defined by respective stages of disease (i.e., I, II, III); and patients with endometriosis (EM) and pelvic benign tumors (BT), all expressed in units/ml.

A standard curve for this sandwich immunoradiometric assay is presented in FIG. 7. The results of this immunoassay for patients and the normal control are presented in FIG. 8 and analyzed in Table 1. (In FIG. 8, "NS" indicates a normal or healthy individual; "OC" is ovarian carcinoma; "CC" is cervical carcinoma, both carcinomas defined by respective disease stages; "EM" is endometriosis; and "BT" is pelvic benign tumor.)

TABLE 1

Serum Levels of CA 215 in Healthy Patients, in Patients with Ovarian and Cervical Carcinoma (by Stages), and in Patients with Endometriosis and Pelvic Benign Tumors (in Unit/ml)

|  | Normal Control | Ovarian Carcinoma Stages | | | Cervical Carcinoma Stages | | | Endometriosis | Pelvic Benign Tumors |
| --- | --- | --- | --- | --- | --- | --- | --- | --- | --- |
|  |  | I | II | III | I | II | III |  |  |
| Cases | 59 | 24 | 7 | 40 | 35 | 18 | 7 | 10 | 23 |
| Mean | 5.47 | 36.2 | 60.2 | 55.0 | 48.0 | 78.6 | 75.7 | 10.2 | 13.6 |
| S.D. | 10.37 | 27.2 | 27.0 | 44.7 | 44.7 | 61.8 | 83.9 | 16.8 | 15.1 |

TABLE 1-continued

Serum Levels of CA 215 in Healthy Patients, in Patients with
Ovarian and Cervical Carcinoma (by Stages), and in Patients
with Endometriosis and Pelvic Benign Tumors (in Unit/ml)

| Normal Control | Ovarian Carcinoma Stages | | | Cervical Carcinoma Stages | | | Endometri- osis | Pelvic Benign Tumors |
| --- | --- | --- | --- | --- | --- | --- | --- | --- |
| | I | II | III | I | II | III | | |

Statistics:
1. Normal Control vs. Ovarian Cancer
Stage I (p < 0.001)
Stage II (p < 0.001)
Stage III (p < 0.001)
Stage I vs. Stages II and III (p < 0.05)
Stages II vs. Stage III (p > 0.05)
2. Normal Control vs. Cervical Cancer
Stage I (p < 0.001)
Stage II (p < 0.001)
Stage III (p < 0.001)
Stage I vs. Stages II and III (p < 0.01)
Stage II vs. Stage III (p > 0.05)
3. Normal Control vs. Endometriosis (p > 0.05)
4. Normal Control vs. Pelvic Benign Tumors (p = 0.05)

It can be demonstrated from this analysis that there are significant differences in serum CA 215 levels between the cancer patients and normal individuals (mean value of 49 U/ml for ovarian cancer, and 60 U/ml for cervical cancer versus 5.5 U/ml for the normal control). Patients with endometriosis and pelvic benign tumor also showed two- to three-fold elevations of serum CA 125 levels, when compared to those of the control. However, the mean serum levels of CA 215 among those groups of patients are considerably lower than those of the cancer patients.

Figure 9:
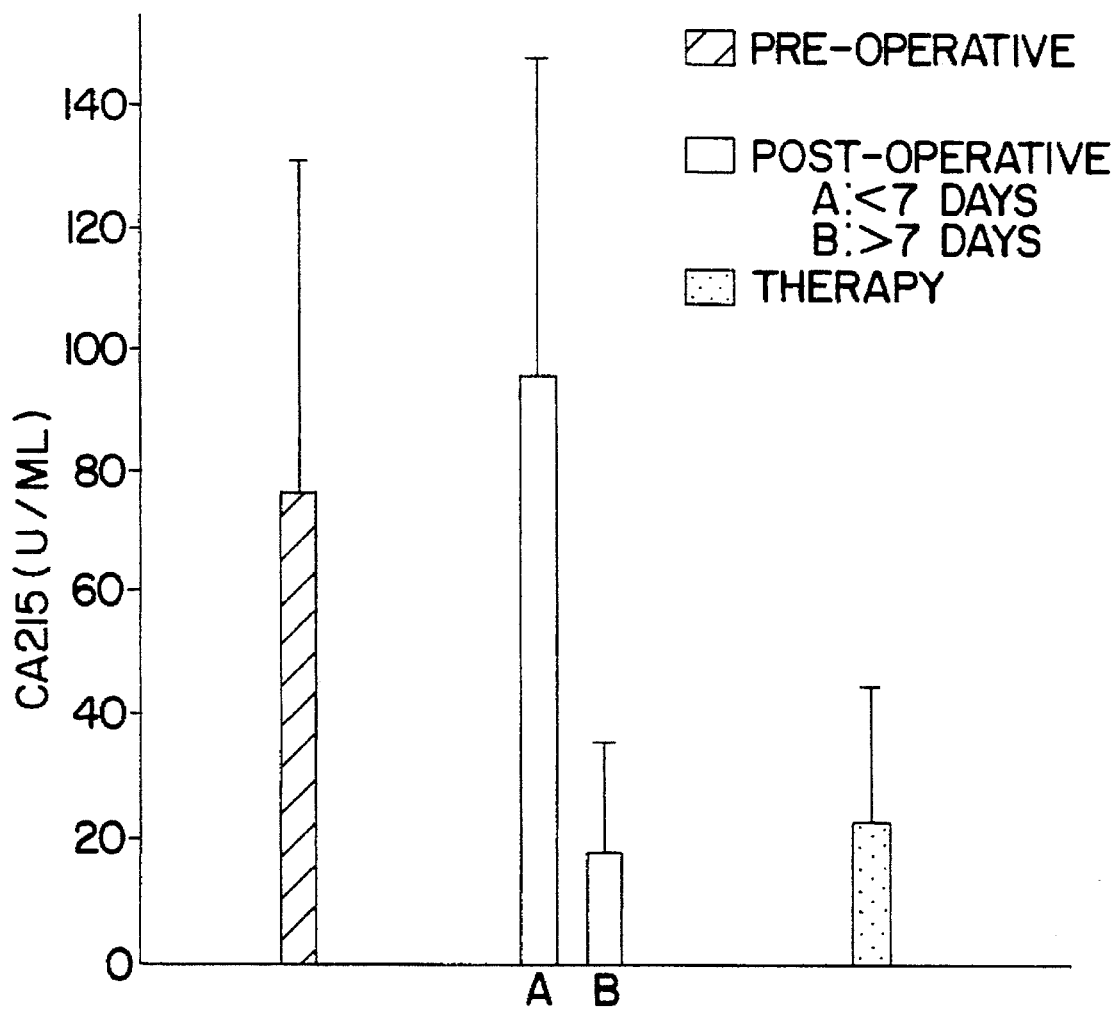
FIG. 9 is a graph which shows a comparison of serum levels of CA 215 among cervical cancer patients at preoperative and postoperative stages and following radiotherapy or chemotherapy.

Serum levels of CA 215 among tumor patients also was correlated with the stages of their respective disease conditions. As shown in Table 1, mean CA 215 levels among tumor patients of all three stages were not only significantly elevated as compared to the control, but also increased significantly with stages of disease progression. For example, in those patients with cervical carcinoma, serum CA 215 levels were correlated with their respective clinical conditions and treatments. Among these patients, serum CA 215 levels were randomly determined at different time intervals, including before the surgical operation, after the operation, and while undergoing radio- or chemotherapy. The mean serum CA 215 remained at relatively high levels during the preoperative stages and during the first seven days following surgery. There was a significant decrease of serum CA 215 levels seven days after surgery and in those patients undergoing radio- or chemotherapy. The results are presented in FIG. 9 and Table 2.

TABLE 2

Comparison of Serum CA 215 Levels in Patients
with Cervical Carcinoma at Preoperative/
Postoperative and Radiotherapy Stages

| | Preoperative | Post-operative* | | Radiotherapy or Chemotherapy |
| --- | --- | --- | --- | --- |
| | | <7 days | >7 days | |
| Case Number | 23 | 5 | 11 | 8 |
| Mean Values (units/ml) | 75.65 | 98.63 | 18.89 | 23.83 |
| S.D. | 56.70 | 57.95 | 18.80 | 22.62 |
| P | | >0.05 | <0.01 | <0.05 |

*Preoperative versus. post-operative cases P < 0.05

Figure 10:
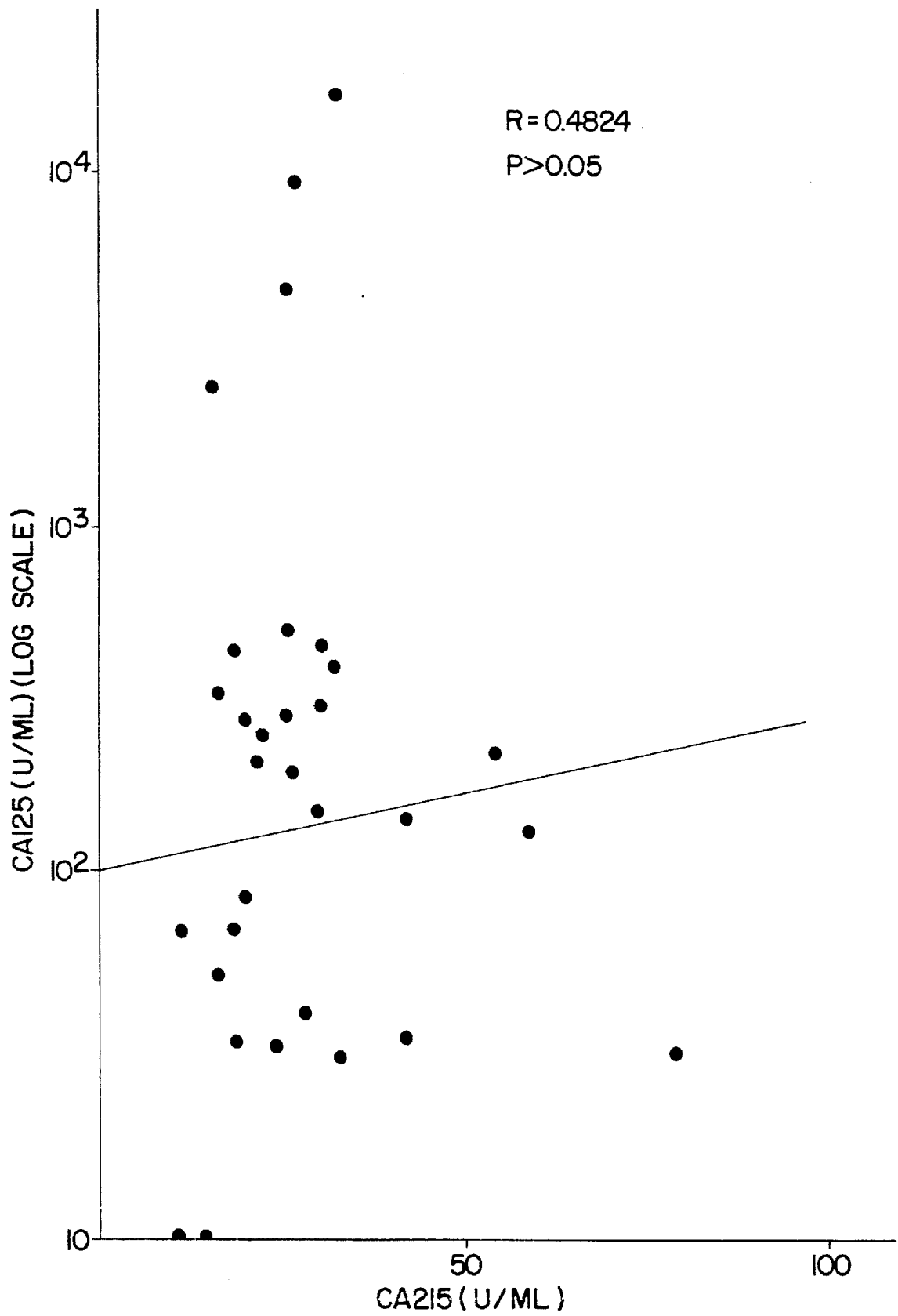
FIG. 10 is a graph which correlates serum levels of CA 215 and CA 125 in 31 patients with ovarian carcinoma.

In thirty-one patients with ovarian carcinoma, serum levels of CA 215 and of CA 125 were determined in parallel in order to determine any correlations between these two tumor markers. As shown in FIG. 10, there was again no apparent correlation between the serum levels of CA 215 and those of CA 125 for a given serum specimen from tumor patients.

Both of these series of studies indicate that serum CA 215 levels in a given patient is associated with tumor size or disease progression and is in parallel response to clinical treatment. Thus, CA 215 is a useful tumor marker for diagnosing and monitoring disease progression in patients with ovarian, cervical, or other carcinomas.

EXAMPLE 4

Characterization of CA 215

Molecular analysis of tumor-associated antigens which react with monoclonal antibodies was performed using the Western blot assay according to the method of Lee, C. Y. G., et al. (1982) Anal. Biochem. 123:14–22. The minimum (or subunit) molecular weight of those antigens reactive to monoclonal antibodies was determined following the assay and detected by autoradiography using Kodak AR-2 film.

Figure 11:
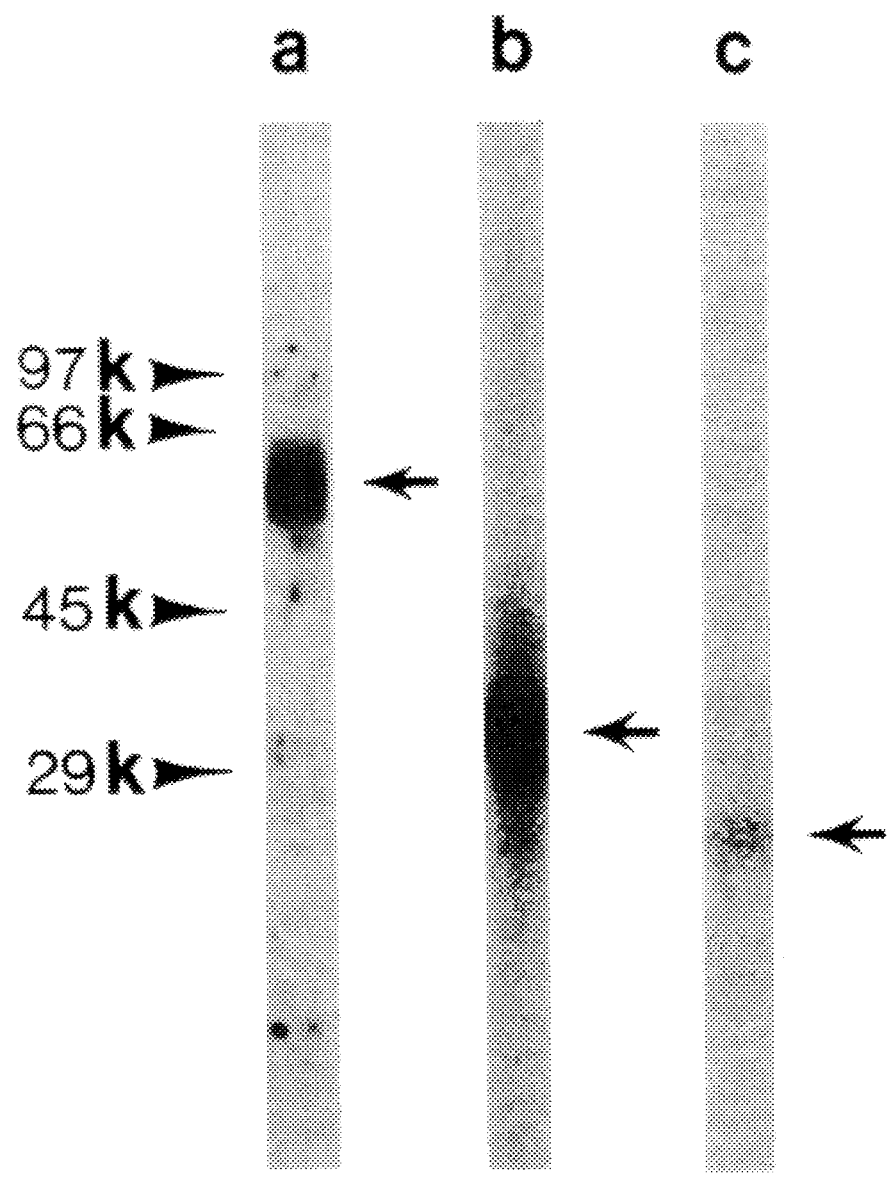
FIG. 11 is a photograph which shows the results of a Western Blot Assay to reveal the molecular weight of the tumor-associated antigens which react with the selected monoclonal antibodies.

Minimal molecular weights of antigens from OC-3-VGH cells reactive to the selected monoclonal antibodies were determined by Western blot and are shown in FIG. 11. Most of these antibodies were found to recognize antigens with molecular weights ranging from 25 to 65 kd. HB 10095 recognizes a tumor-associated antigen (CA 215) with a minimal molecular weight of 60 kd on the SDS gels.

The native molecular weight of tumor-associated antigen, CA 215, was determined by Sephacryl S-300 gel filtration chromatography. Myoglobin (mol. wt. 13,000), ovalbumin (mol. wt. 45,000), immunoglobulin G (mol. wt. 160,000), and thyroglobulin (mol. wt. 675,000) were used as molecular weight standards. The supernatant of sonicated OC-3-VGH cells ($1 \times 10^6$ cells/ml) was recovered by centrifugation and loaded on a Sephacryl S-300 gel filtration column (1×30 cm). Fractions of 0.3 ml were collected and assayed to determine the amount of CA 215 present using the established sandwich immunoradiometric assay as described in Example 3, supra. Using Sephacryl S-300 gel filtration chromatography, CA 215 was shown to exist as aggregates with molecular weights ranging from 100 kd to 2000 kd.

Figure 12:
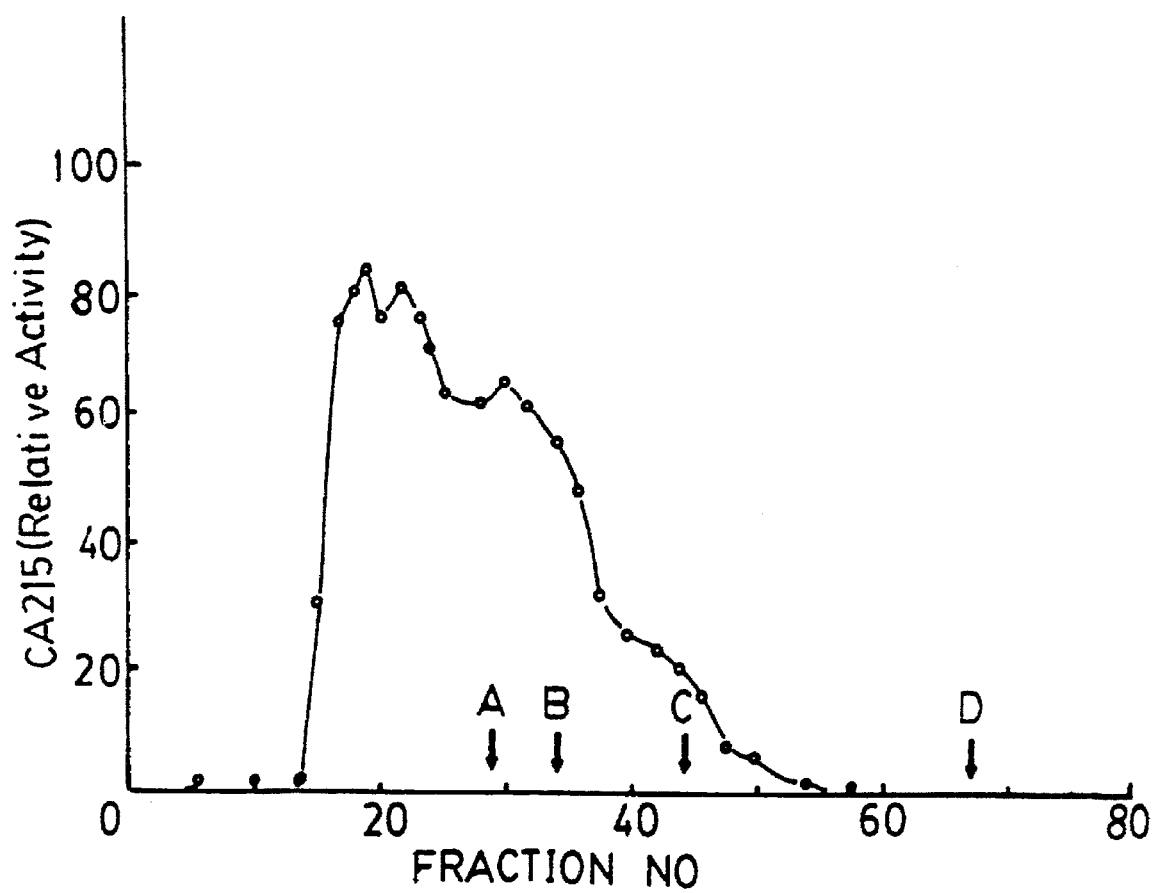
FIG. 12 is a chart which shows the elution profile of Sephacryl S-300 gel filtration chromatography to determine the native molecular weight of the tumor-associated antigen CA 215 reactive to monoclonal antibody HB 10095.

CA 215 was purified by a single-step immunoaffinity chromotographic procedure using HB 10095 antibody as the affinity ligand. CA 215 can be purified either from the extract of cultured OC-3-VGH tumor cells or from the shed medium recovered from the in vitro culture of OC-3-VGH cells. During the course of antigen purification, the immunoactivity of CA 215 was monitored by the established dot-blot radioimmunoassay (Zhu et al., in press). Briefly, the soluble extract from 1×10⁷ OC-3-VGH cells or from 100 ml of the shed medium was loaded on an immunoaffinity column (1.5×6 cm; Sepharose 4B coupled with purified HB 10095 equilibrated with phosphate buffered saline (PBS) at room temperature. The column was washed extensively with PBS containing 0.5M NaCl until the absorbance at 280 nm decreased to the blank level. CA 215 activity was then eluted with a solution containing 50 mM glycine-HCl, pH 2.2. The elution profile of this antigen from a gel filtration column is shown in FIG. 12. The first protein peak was pooled and analyzed for purity by SDS gel electrophoresis and for immunoactivity using dot-blot immunoassay for immunoactivity. The presence of CA 215 in the purified protein band was verified by the Western blot assay. Purification from the shed medium or from extract of cultured OC-3-VGH cells was from 250–500 fold to homogeneity.

Deposit of Biological Materials

The following materials were deposited with American Type Culture Collection (ATCC), 12301 Parklawn Drive, Rockville, Md. 20852, U.S.A. These deposits will be maintained under the terms of the Budapest Treaty on the deposit of microorganisms. In the event of a discrepancy between a description of the deposit herein and the deposited material itself, the deposited material is controlling. The deposit of such material, or its availability, is not the grant of a license to make, use, or sell any of the deposited materials.

| Material | ATCC Accession Number | Deposit Date |
|---|---|---|
| RP 215 | HB 10095 | 5 April 1989 |

While the present invention has been illustrated above by certain specific embodiments, the specific examples are not intended to limit the scope of the invention as described in the appended claims.

I claim:

1. The monoclonal antibody which specifically binds with a tumor-associated antigen CA215 and which is produced by the hybridoma ATCC HB 10095, or an antigen-binding fragment of said antibody.

2. The antibody or fragment off claim 1 covalently bound to a label.

3. The antibody or fragment off claim 2 wherein the label is a radiolabel.

4. The antibody or fragment of claim 3 wherein the radiolabel is selected from the group consisting of $^{131}$I, $^{125}$I, $^{123}$I, $^{99}$Tc, $^{67}$Ga and $^{111}$In.

5. An antibody producing cell deposited under ATCC Accession No. HB 10095, and the progeny thereof.

6. The fragment of claim 1 which is an Fab or F(ab')$_2$ fragment.

* * * * *